(12) United States Patent
Paulussen et al.

(10) Patent No.: US 7,666,478 B2
(45) Date of Patent: Feb. 23, 2010

(54) BIOMOLECULE IMMOBILISATION USING ATMOSPHERIC PLASMA TECHNOLOGY

(75) Inventors: Sabine Paulussen, Antwerp (BE); Winnie Dejonghe, Tervuren (BE); Jan Meneve, Mol (BE); Ludo Diels, Oelegem (BE)

(73) Assignee: Vlaamse Instelling Voor Technologisch Onderzoek (VITO), Mol (BE)

( * ) Notice: Subject to any disclaimer, the term of this patent is extended or adjusted under 35 U.S.C. 154(b) by 74 days.

(21) Appl. No.: 11/587,525

(22) PCT Filed: Apr. 29, 2005

(86) PCT No.: PCT/BE2005/000062

§ 371 (c)(1),
(2), (4) Date: Aug. 3, 2007

(87) PCT Pub. No.: WO2005/106477

PCT Pub. Date: Nov. 10, 2005

(65) Prior Publication Data

US 2007/0292972 A1     Dec. 20, 2007

(30) Foreign Application Priority Data

Apr. 30, 2004  (EP) ............................. 04447109

(51) Int. Cl.
*H05H 1/24*   (2006.01)
*C12Q 1/00*   (2006.01)
*G01N 33/53*  (2006.01)
*C23C 16/00*  (2006.01)

(52) U.S. Cl. ................ 427/569; 427/576; 427/578; 435/4; 435/7.1; 118/715; 118/723 R; 118/723 E

(58) Field of Classification Search ............ None
See application file for complete search history.

(56) References Cited

FOREIGN PATENT DOCUMENTS

| DE | 198 35 869 A1 | | 2/2000 |
|---|---|---|---|
| EP | 0 351 950 A2 | | 1/1990 |
| EP | 1073091 | * | 1/2001 |
| EP | 1 231 470 A1 | | 8/2002 |
| WO | 03/086031 A1 | | 10/2003 |
| WO | WO2004/028220 | * | 4/2004 |

OTHER PUBLICATIONS

Paulussen et al. "Antimicrobial coatings obtained in an atmospheric pressure dielectric barrier glow discharge" Mrs Symposium Proceedings Series vol. 724 Apr. 1, 2002 X-002347059.

Muguruma et al. "Plasma-polymerized films for biosensors" Trends in analytical Chemistry vol. 18, No. 1 p. 62-68 (1999).

* cited by examiner

*Primary Examiner*—N. Yang
*Assistant Examiner*—Leon Y Lum
(74) *Attorney, Agent, or Firm*—Merchant & Gould P.C.

(57) ABSTRACT

The present invention is related to a method for immobilising a biomolecule on a surface by generating and maintaining an atmospheric pressure plasma, the method comprising the steps of: introducing a sample in the space between two electrodes, a mixed atmosphere being present between the electrodes, applying an alternating voltage to the electrodes for generating and maintaining a plasma in the volumetric space between the electrodes, characterized in that the mixed atmosphere comprises an inert gas or nitrogen, an aerosol comprising a reactive precursor and an aerosol comprising a biomolecule, the reactive precursor and biomolecule being deposited and immobilized during the depositing step.

19 Claims, No Drawings

BIOMOLECULE IMMOBILISATION USING ATMOSPHERIC PLASMA TECHNOLOGY

FIELD OF THE INVENTION

The present invention is related to plasma techniques, involving the inclusion of biological molecules into a plasma deposited layer.

STATE OF THE ART

It is known in the art to apply functional groups to a surface via plasma technology. In a second step, it is then possible to attach biomolecules to said functional groups. The functional groups can be obtained by activation of polymers or by application of a cover layer with functional groups. In most cases, the known technology relates to at least a two-step process.

DE19835869 describes the stabilisation of immobilised enzyme on a substrate, especially a biosensor or bioreactor. The document mentions simultaneous application of enzymes on a surface and application of a polymer layer. The technology used is gas-phase deposition, which creates a harsh environment for the biomolecules and leads to unwanted degradation thereof.

EP0351950 relates to the use of plasma to immobilise protein on polymeric surfaces, wherein a two-step process is used wherein biomolecules are exposed to a low-pressure (vacuum) plasma. Application of biomolecules is done separately from application of polymerprecursors. The described process is thus only applicable to polymer substrates.

EP1231470 describes a method for immobilising substances with plasma technology. Biomolecules are brought in contact with plasma in at least a two-step process: an optional plasmapolymerlayer is applied to a surface followed by spreading the biomolecules on said surface and application in vacuo of a plasmapolymerfilm on said biomolecules. It is doubtful that the biomolecules retain their activities with this method, as they are covered by a thick polymer film.

WO 03/086031 describes an atmospheric plasma process comprising spraying liquid precursors in a plasma causing polymerisation. No specific mention is made of biomolecules.

AIMS OF THE INVENTION

The present invention aims to provide a method to immobilise biomolecules on a surface so as to be able to use said biomolecules in specific interaction with other molecules of interest. The object of the present invention is thus to develop an entirely new, one-step process for the immobilisation of proteins/enzymes or other biomolecules, which is applicable on a large scale to surfaces of any kind. The new methodology should offer several advantages over the classical immobilisation techniques, including a better reproducibility, high flexibility, broad applicability, straightforward processing and thus high throughput rates. The new way of processing may in turn lead to entirely new applications that are not feasible with the current state-of-the-art technology.

SUMMARY OF THE INVENTION

The present invention is related to a method for immobilising a biomolecule on a sample surface by generating and maintaining a cold atmospheric pressure plasma, said method comprising the steps of:
  introducing a sample in the space between a first and a second electrode, a mixed atmosphere being present between said electrodes,
  applying an alternating voltage to said first and second electrode for generating and maintaining a plasma in the volumetric space between said electrodes, said voltage alternating between a positive voltage for said first electrode and a zero voltage for said second electrode, and a zero voltage for said first electrode and a negative voltage for said second electrode, and
  depositing a coating on a surface of said sample,
wherein a reactive precursor and a biomolecule are deposited and immobilised during the depositing step.

Preferably, the reactive precursor is a gas or a liquid in the form of an aerosol.

Preferably, the biomolecule is selected from the group consisting of a protein, a polynucleotide, a sugar, a lipid, a growth factor, a hormone and a physiologically active substance.

The reactive precursor can be selected from the group consisting of a hydrocarbon, a fluorinated hydrocarbon and an organometallic compound or a combination thereof.

The mixed atmosphere can comprise helium, argon, nitrogen, air, carbon dioxide, ammonium or a combination thereof.

The sample can comprise metal, ceramic or plastic materials, woven or non-woven fibres, natural fibres or synthetic fibres or powders.

If necessary, the electrodes can be cooled to temperatures between 0° C. and 100° C.

In a first embodiment of the present invention, the mixed atmosphere comprises the reactive precursor and an aerosol comprising the biomolecule.

In an alternative embodiment of the present invention, said method further comprises the steps of:
  applying a solution containing said biomolecule onto a sample surface,
  introducing said sample in the space between the first and second electrode or in the afterglow of the plasma which is maintained between the two electrodes, a mixed atmosphere being present between said electrodes,
  applying an alternating voltage to said first and second electrode for generating and maintaining a plasma in the volumetric space between said electrodes, said voltage alternating between a positive voltage for said first electrode and a zero voltage for said second electrode, and a zero voltage for said first electrode and a negative voltage for said second electrode, and
  depositing a coating on a surface of said sample, wherein said mixed atmosphere or its afterglow comprises the reactive precursor, which is deposited onto the sample surface during the depositing step.

The step of applying the solution containing the biomolecule onto a sample surface is preferably selected from the group consisting of spreading out of the solution followed by drying, adsorption and covalent linking with or without making use of spacer molecules.

In another alternative embodiment of the present invention, the reactive precursor is administered to the afterglow of said plasma together with an aerosol comprising a biomolecule, both of which are deposited and immobilized onto a sample surface which is positioned in the same afterglow during the depositing step.

DETAILED DESCRIPTION OF THE INVENTION

The present bio-engineered materials are envisioned to have bio-recognition sites designed to specifically interact with other biological or non-biological species of interest.

The present invention allows to design and construct robust bio-engineered surfaces by cold, atmospheric plasma treatment, which allows the binding of all kinds of biomolecules to surfaces in a direct way without using chemical linkers that can change the configuration and activity of biomolecules or that may lead to high costs and problems concerning homogeneity. This technology can pave the way to a whole new realm of future applications in the medical, chemical, environmental, food, materials and many other industrial sectors, including but not limited to:

- Biosensors for large and small-scale applications like for instance the detection of pollutants (dioxins, pseudo-estrogenic substances, antibiotics, micro-pollutants, etc. e.g. in water and air), biomedical diagnostics, toxicity tests etc.;
- Labs-on-a-chip: the low energy barrier to mobility in the plane of the surface can be used to facilitate complex reactions that require a cluster of different proteins, including applications in the field of molecular biology;
- Bio-mimetic materials e.g. for implants (mimicking bio-molecular recognition);
- Solar-cells based on immobilised photosensitive charge transfer proteins;
- Non-fouling surfaces for medical diagnostics, heat exchangers, and food processing equipment;
- Anti-microbial coatings for (medical) textile, plastics for medical applications, food packaging;
- Surfaces for directing controlled drug release;
- Intelligent materials/textiles, e.g. by incorporating proteins in conducting plasma polymer coatings, which may allow transmission of a biological signal to a processor;
- Templates for extra-corporeal and/or in-vivo growth of functional tissues;
- Bio-induced crystalline morphologies: biomolecules ordered on a surface may induce mineralisation and the morphologies formed differ from the classical ones. Such mineral surfaces may find applications in materials development and micro-electronics;
- Conducting coatings based on conducting proteins (like e.g. cytochrome C en bovine serum albumin);
- Bio-catalysis applications e.g. biodegradation of very recalcitrant molecules in wastewater and removal of micro-pollutants, catalysis of very specific biochemical reactions for producing high value chemical compounds (e.g. chiral compounds).

Stable solutions of biomolecules are administered to a cold atmospheric plasma together with a plasmapolymer precursor, either a gas or a liquid. The biomolecules such as proteins, enzymes, nucleic acids and sugars can be in aqueous solution or in a precursor solution. If necessary, aerosols of mixtures or mixtures of different aerosols can be added to the plasma, possibly together with gaseous precursors. Alternatively, stable solutions of biomolecules are arranged onto the surface of a sample prior to applying a thin polymer layer on said surface by a cold atmospheric plasma treatment with either liquid or gaseous precursor molecules. It is important to incorporate the biomolecules in a polymer coating in such a way that at least part of the biological activity or structure is retained. The present invention constitutes a one-step process. Furthermore, any substrate, of any form or material, can be coated with biomolecules using the method of the present invention.

A major advantage of the present invention is its ability to treat materials in a cost-effective way and at a large scale, which is not feasible with the current state-of-the-art technology.

The method of immobilisation according to the present invention comprises the incorporation of biomolecules, and proteins in particular, in thin plasma polymerised coatings. For this purpose, solutions containing these proteins or other biomolecules will be administered to a cold atmospheric plasma together with either liquid or gaseous polymer precursors. Alternatively the solutions containing these proteins can be arranged onto the surface of a substrate prior to administering the sample to a cold, atmospheric plasma together with either liquid or gaseous polymer precursors. The preferred plasma configuration to be used in practising this invention is the dielectric barrier discharge (DBD), which consists of a uniform glow. Immobilisation of biomolecules is not feasible with the well-established vacuum or low pressure RF (13.56 MHz) plasma technology for a number of reasons but mainly because of the presence of highly energetic species in the plasma which cause considerable damage to proteins or may even destroy them. In addition, processing of proteins and protein solutions is impracticable under vacuum conditions.

Plasma processing at atmospheric pressure is a relatively new technology—the first reports date from 1990—and it offers many advantages over vacuum plasma technology, including the ability to work in-line, the significantly lower process costs and the compatibility with virtually any type of substrate material. The most important feature of atmospheric pressure plasmas in this context is however the absence of highly energetic species in the plasma. While complex precursor molecules get fractured when exposed to vacuum plasma, they retain their structure to a high extent in atmospheric pressure plasmas. The latter phenomenon is attributed to the reduced mean free path length of the active species due to the presence of high amounts of gas molecules. Accordingly this new technology also allows the incorporation of biomolecules into coatings with only minor modifications. Solutions containing biomolecules/proteins, either aqueous or with solvents added, can be administered to the plasma as an aerosol together with a liquid or gaseous hydrocarbon or hybrid organic/inorganic molecule polymer precursor. Accordingly, biomolecules present in the droplets may be incorporated into thin plasma polymer coatings where they are exposed to the surface and exhibit their activity. Alternatively, the solutions containing biomolecules/proteins are applied onto the surface of a sample prior to administering them to a cold, atmospheric plasma, where a thin layer with a thickness of a few nanometers is deposited on top of the biomolecules. The incorporation of biomolecules may be accomplished physically (by embedding) or by covalent linking, depending on the reaction conditions and the type of precursor used. During this process, proteins will not be forced to change their conformation in order to bind to a surface because the coating, preferably a coating with a high water content, will be formed around the proteins, thus stabilising and protecting them. It remains however important that the orientation of the proteins near the surface allows them to expose their biologically active sites or that the cross-link density of the plasma polymer is sufficiently low to allow diffusion of the matching substrates to completely embedded proteins. Precursors that contain functional groups like amines and carboxyls will chemically bind to biomolecules while this is less likely to occur with precursors like alkanes. In the latter case embedding of proteins in a coating may occur. The precursors include organic molecules (like acrylic compounds, alkanes, alkenes, etc.) and organic/inorganic hybrid molecules (like HMDSO and TEOS).

Moreover, apart from the presence of low energy radicals, reaction conditions in cold, non-equilibrium plasmas are very mild: low temperature (room temperature up to 60° C.) and ambient pressure. So far, no literature or patents have been published on the manufacture of similar biofunctional coatings by atmospheric pressure plasma technology.

EXAMPLE 1

A plasma discharge at atmospheric pressure is obtained between two horizontally placed parallel electrodes with a size of 45×45 mm, both covered with an alumina ($Al_2O_3$) plate of 2 mm thickness. The distance between the covered electrodes is 2 mm. The top electrode is grounded. The bottom electrode is connected to a variable frequency AC power source (ENI, model RPG-50). The frequency of the AC power source is set at 2 kHz. In order to perform tests in a controlled environment, the electrode configuration is mounted in a closed chamber that is evacuated and subsequently filled with the carrier gas before deposition is started.

Helium is used as carrier gas. The flow rate of the carrier gas is controlled by a mass flow controller and set at 20 l/min. Hexamethyldisiloxane (HMDSO) is used as reactive precursor. It is added to the inert carrier gas in the form of an aerosol. Another aerosol, containing an aqueous solution of streptavidin, is added simultaneously to the plasma. The deposition time is set at 1 min. Coating deposition is observed at the surface of both electrodes and on the substrates attached to these electrodes. The thickness of the coatings equals 175 nm. The presence of streptavidin in the plasmapolymer coating obtained and the ability of streptavidin to bind to fluorescently labelled biotin after immobilisation were evaluated using fluorescence microscopy. After using fluorescently labelled biotin binding-assay, a signal could be observed, which indicates that streptavidin was immobilized into the coating, while retaining at least part of its binding activity.

EXAMPLE 2

A cold, atmospheric pressure plasma discharge is obtained between two horizontally placed parallel electrodes with a size of 8×15 cm, both covered with float glass plate of 3 mm thickness. The distance between the electrodes is 2 mm. The bottom electrode is grounded and connected to a Peltier element which can provide cooling to room temperature, if necessary. The Peltier element is in turn connected to a cooling fin which is cooled by a fan. The top electrode is connected to a variable frequency AC power source. An AC-field of 8 kHz and 20 kV is applied to the electrodes.

Helium is used as a carrier gas. The flow rate of the carrier gas is controlled by a mass flow controller and set at 6 l/min. Acetylene is used as reactive precursor. It is mixed with the inert carrier gas and administered to the plasma at a flow rate of 0.3 l/min. An aerosol, containing an aqueous solution of avidin, is added simultaneously to the plasma. The deposition time is set at 30 seconds. A coating is deposited on the surface of both electrodes and on the glass and silicon substrates attached to the electrodes. The thickness of the coating equals 25 nm as determined by scanning electron microscopy (SEM) analysis of cross-sections of the coated silicon substrates. The presence of avidin in the plasmapolymer coating obtained and the ability of avidin to bind to fluorescently labelled biotin after immobilisation were evaluated using fluorescence microscopy. After using fluorescently labelled biotin binding-assay, a signal could be observed, which indicates that avidin was immobilized into the coating, while retaining at least part of its binding activity. Grazing-incidence small-angle-X-ray scattering analysis (GISAX) was carried out in order to obtain information on the structure and size of the immobilised avidin. Apparently at least part of the immobilized avidin has retained its original structure and shape, and thus its activity.

EXAMPLE 3

The method described in example 2 was repeated using a liquid precursor, being pyrrole, instead of acetylene. Pyrrole was administered to the plasma zone as an aerosol. Again, coating deposition was observed on the surface of both electrodes and on the glass and silicon substrates attached to their surface. The coating thickness equaled 35 nm after 30 seconds of deposition.

EXAMPLE 4

The reactor set-up described in example 2 was used for the immobilization of bovin serum albumin (BSA). Helium was administered to the plasma zone at a flow rate of 6 l/min. Pyrrole is used as reactive precursor. It is added to the inert carrier gas as an aerosol. Another aerosol, containing an aqueous solution of BSA is simultaneously added to the plasma. An AC-field of 2 kHz and 20 kV is applied to the electrodes. The deposition time is set at 30 seconds. A coating is deposited on the surface of both electrodes and on the glass and silicon substrates attached to the electrodes. The thickness of the coating equals 35 nm as determined by scanning electron microscopy (SEM) analysis of cross-sections of the coated silicon substrates. Grazing-incidence small-angle-X-ray scattering analysis (GISAX) was carried out in order to obtain information on the structure and size of the immobilized BSA. Apparently, a substantial part of the immobilized BSA has retained its original structure and shape, and thus its activity.

EXAMPLE 5

A solution of bovin serum albumin (BSA) is spread out onto a glass substrate. After drying the sample for 12 hours at room temperature, it is placed on the lower electrode of the set-up described in example 2. Helium and acetylene are administered to the zone between the electrodes at a flow rate of 6 and 0.3 l/min, respectively. After 10 seconds of deposition, a layer with a thickness of 3 to 5 nm was obtained. The sample was analyzed by means of grazing-incidence small-angle-X-ray scattering analysis (GISAX) and apparently, BSA has retained its original structure and size to a high extent after this type of treatment.

The invention claimed is:

1. A method for immobilising a biomolecule on a surface of a sample comprising:
   introducing said sample in a volumetric space between a first and a second electrode, a mixed atmosphere being present between said electrodes, said mixed atmosphere comprising a reactive precursor, an inert gas or nitrogen, and an aerosol comprising the biomolecule;
   applying an alternative voltage difference between said first and second electrode, one electrode being grounded and the other electrode being connected to an alternative voltage;
   generating and maintaining a cold atmospheric pressure plasma in the volumetric space between said electrodes; and
   depositing a coating on said surface of said sample, thus immobilizing said biomolecule.

2. The method according to claim 1 wherein the reactive precursor is a gas or a liquid in the form of an aerosol.

3. A method for immobilising a biomolecule on a surface of a sample comprising:

introducing a sample in a volumetric space between a first and a second electrode, a mixed atmosphere comprising an inert gas or nitrogen being present between said electrodes;

applying an alternating voltage difference between said first and second electrodes, one electrode being grounded and the other electrode being connected to an alternating voltage;

generating and maintaining a cold atmospheric pressure plasma in the volumetric space between said electrodes, the plasma comprising an afterflow;

positioning said sample in said afterflow;

introducing a reactive precursor and an aerosol comprising the biomolecule into said afterflow of said plasma; and depositing a coating on said surface of said sample, thus immobilizing said biomolecule.

4. The method according to claim 1, wherein the biomolecule is selected from the group consisting of a protein, a polynucleotide, a sugar, and a lipid.

5. The method according to claim 1, wherein the reactive precursor is selected from the group consisting of a hydrocarbon, a fluorinated hydrocarbon, an organometallic compound, and a mixture thereof.

6. The method according to claim 1, wherein the mixed atmosphere comprises helium, argon, nitrogen, air, carbon dioxide, ammonium, or a mixture thereof.

7. The method according to claim 1, wherein the sample comprises metal, ceramic material, or plastic materials.

8. A method according to claim 1, wherein the electrodes are cooled to temperatures between 0° C. and 100° C.

9. The method according to claim 3, wherein the biomolecule is selected from the group consisting of a protein, a polynucleotide, a sugar, and a lipid.

10. The method according to claim 3, wherein the biomolecule is a growth factor or a hormone.

11. The method according to claim 3, wherein the reactive precursor is selected from the group consisting of a hydrocarbon, a fluorinated hydrocarbon, an organometallic compound, and a mixture thereof.

12. The method according to claim 3, wherein the mixed atmosphere comprises helium, argon, nitrogen, air, carbon dioxide, ammonium, or a mixture thereof.

13. The method according to claim 3, wherein the sample comprises metal, ceramic material, or plastic material.

14. The method according to claim 3, wherein the sample comprises, woven fibre, non-woven fibre, or powder.

15. The method according to claim 3, wherein the sample comprises a natural fibre or a synthetic fibre.

16. The method according to claim 3, wherein the electrodes are cooled to temperatures between 0° C. and 100° C.

17. The method according to claim 1, wherein the biomolecule is a growth factor or a hormone.

18. The method according to claim 1, wherein the sample comprises a woven fibre, a non-woven fibre, or a powder.

19. The method according to claim 1, wherein the sample comprises a natural fibre or a synthetic fibre.

* * * * *